(12) United States Patent
Cornelli et al.

(10) Patent No.: US 6,569,462 B1
(45) Date of Patent: May 27, 2003

(54) LAYERING PROCESS FOR MULTIPARTICULATE DOSAGE FORM

(75) Inventors: Livio Maria Cornelli, Pandino (IT); Giovanni La Grasta, Torri di Quartesolo (IT); Marco Giuseppe Raffaele Marconi, Cinisello Balsamo (IT)

(73) Assignee: Eurand International S.p.A. (IT)

( * ) Notice: Subject to any disclaimer, the term of this patent is extended or adjusted under 35 U.S.C. 154(b) by 0 days.

(21) Appl. No.: 09/701,233

(22) PCT Filed: May 21, 1999

(86) PCT No.: PCT/EP99/03512

§ 371 (c)(1),
(2), (4) Date: Jan. 16, 2001

(87) PCT Pub. No.: WO99/61006

PCT Pub. Date: Dec. 2, 1999

(30) Foreign Application Priority Data

May 22, 1998 (EP) .............................................. 98109349

(51) Int. Cl.[7] .............................. A61K 9/16; A61K 9/50; A61K 9/32; B05D 1/36; B05D 7/00

(52) U.S. Cl. ...................... 424/497; 424/480; 424/482; 424/490; 424/494; 427/402; 427/407.1

(58) Field of Search ................................ 424/490, 497, 424/494, 482, 480; 427/402, 407.1

(56) References Cited

U.S. PATENT DOCUMENTS

| 4,702,932 | A | * | 10/1987 | Cosentino et al. |
| 5,470,603 | A | * | 11/1995 | Staniforth et al. |
| 5,505,983 | A | * | 4/1996 | Kamada |
| 5,618,562 | A | * | 4/1997 | Saito et al. |

FOREIGN PATENT DOCUMENTS

| WO | 9514460 | 6/1995 |
| WO | 9601621 | 1/1996 |

* cited by examiner

Primary Examiner—Thurman K. Page
Assistant Examiner—Simon J. Oh
(74) Attorney, Agent, or Firm—Thompson Hine LLP (57) ABSTRACT

The present invention relates to a new layering process, in particular to a process for the manufacture of multiparticulate solid oral dosage forms based on a dry spray layering technique optionally with electrostatic attraction. The invention also relates to an apparatus for use in the process.

21 Claims, 4 Drawing Sheets

LAYERING PROCESS FOR MULTIPARTICULATE DOSAGE FORM

BACKGROUND OF THE INVENTION

Layering processes involve loading solid inert cores with drugs and/or excipients. Inert cores, placed in a suitable vessel such as a coating pan or a fluid bed, may be layered according to different methods. Some methods consist of spraying onto the cores a solution/suspension containing both drug and binding agent. Others are based on layering the drug directly in powdery form where drug loading occurs by gravity and adhesion is ensured by a liquid binder sprayed onto the cores. Some examples concerning different layering processes are described in the following patents: WO 95/14460, WO 96/01621.

The layering process is particularly suitable for production of small drug loaded units, multiples of which are placed into capsules for patient delivery. In the case of spherical inert cores such as non pareils, the layering techniques from solution/suspensions, produce homogeneous drug loaded particles, which retain an approximately spherical shape. They are therefore particularly suitable for successively film coating to build up the particle with the aim of providing a desired drug release profile. These spraying methods based on liquid applications are very time consuming due to the relative low concentration of the active substance in the liquid vehicle and the need to evaporate large amounts of solvent. In addition they are subject to process and product variables. Also it is preferable that liquid layering methods are based on aqueous systems; nevertheless organic solvents are often used for those active substances having poor aqueous solubility. A process using organic solvent has disadvantages of high costs, environmental pollution and explosion hazard. Drug state transitions can also occur either during or after the liquid spraying phase. As a result, crystalline drugs once loaded on inert cores, may assume a different crystalline state or even a metastable amorphous state, both altering the drug release profile on storage.

Known powder layering techniques based on drug loading by gravity overcome some of the above-mentioned drawbacks. However limiting factors accompany the use of powder layering such as non-uniform distribution of the drug onto the seeds, and high dust formation during the process which lowers the yields and requires the process to be run discontinuously with intermediate drying. This is necessary to avoid sticking or agglomeration of individual cores. but is very time consuming if an adequately deep layer is to be loaded onto the cores. A typical industrial process may take in the order of 24 hours.

The non-uniform drug distribution gives rise to single loaded units with irregular shape and rough surface and causes an increment of the products surface specific area (SSA). An increase of the SSA means a higher spray volume must be applied to get the desired average thickness. Poor reliability from batch to batch is also associated with such a layering system. Moreover, when coating is based on weight gain, the poor batch reproducibility gives rise to finished products with a variable average film thickness and therefore the resulting units will each have different release profiles. Where a final sealing coating is required, the volume of sealant is increased due to high surface area of the units.

Additionally, known powder layering techniques produce a rather considerable dust formation which tends to be suspended on the air stream during the process. This dust problem is also responsible for cross-contamination and safety hazards for the operators, as well as loss of active substance through the exhaust of the ventilation system.

Another disadvantage of powder layering is that the poor reliability requires time-consuming procedures to get satisfactory results in matter of process validation. This is necessary to meet requirements of medicine control agencies.

There is need therefore for a process for applying a drug or excipient layer to a unit or seed particle with improved layering times over solution/suspension coating techniques.

There is also a need for a process to prepare spherical dosage forms with improved regularity of shape.

Furthermore there is a need for a process for preparing multiple units dosage forms with consistent properties and improved reliability of the units.

The present invention provides a process for applying a layer to a pharmaceutical unit, such as a seed unit or tablet, which comprises:

(a) spraying the unit with dry particles of drug and/or excipient, (b) applying to the unit a binder comprising solvent, and (c) drying.

Steps (a) and (b) can be initiated, and/or terminated, sequentially in either order or simultaneously. Generally once the process has started steps (a) and (b) are run simultaneously for sufficient time to load the desired amount of drug onto the pellet. During simultaneous loading (ie steps (a) and (b) running for a period together) it is possible to reach an equilibrium where solvent evaporates or dries at a rate substantially equal to the rate of binder application.

Conveniently the binder is applied before the powder application starts, for example about 20 seconds or less before, eg about 10 seconds before, and is terminated preferably after the powder spraying has stopped to ensure all drug has been applied and to minimise loss. Drying may continue until substantially all solvent is removed.

Powder atomisation ensures a homogeneous drug loading and an enhanced sphericity.

In one aspect of this invention when coating the unit with particles of drug and/or excipient; the unit and the particles are at different electrical potentials such that electrostatic attraction occurs between them;

Optionally, the dry particles may be electrically charged with respect to the unit.

Accordingly this invention also provides a process for applying a layer to a pharmaceutical unit (eg seed or tablet) which comprises:

(a) spraying the unit with dry particles of drug and/or excipient, the unit and the particles being at different electrical potentials such that electrostatic attraction occurs between them;

(b) applying to the unit a binder, and (c) drying.

As above steps (a) and (b) can be carried out, and/or initiated, sequentially in either order or simultaneously.

Spraying in the manner described herein permits layering to substantially the whole surface of the unit in a single operation.

Electrostatic attraction can minimise dust formation, and thus there is reduced loss of active substance through the exhaust of the ventilation system. Furthermore, the particles are strongly attracted to the seed units, and consequently the volume of particles carried off during evaporation of the binder is reduced. However an electric charge is unsuitable in cases where an organic solvent is used for the binder, and accordingly, in such cases the invention can be used without applying a charge.

The present invention is particularly suitable for the production of pharmaceutical units with high drug loading. Such a method ensures high reliability while improving the productivity in comparison with known powder layering processes. It finds broad applicability on drug loading of inert cores such as non pareils seeds or granules on the manufacturing of multiparticulate dosage forms. Layering of monolithic dosage forms such as tablets is however possible, eg tablets up to about 20 mm in length. Drug particles are sprayed through a nozzle connected with an air flow inlet. Particles are thus atomized onto inert seeds loaded on conventional equipments such as for instance coating pans beds. This system ensures uniform layering, and improved process productivity in comparison with known powder layering techniques based on gravity loading when processing the same quantity of components in the same coating bowl.

Preferably the powder and binder are applied from different directions, or in the same direction but along separate axes. This can avoid over wetting and thus sticking or aggolmeration. As a result process time can be reduced significantly being strictly dependent on spraying rates of powder and binder.

The potential difference between the unit and the particles, if applied, should be sufficiently high to ensure a strong attraction between the two and may conveniently be in the order of from about 50,000 to about 300,000 volts, preferably about 75,000 to 200,000 volts. Since it is not necessary for both the unit and the particles to be electrically charged the process may be conveniently carried out by electrostatically charging one of the unit and the particles. Preferably the particles are electrostatically charged, most preferably with a negative charge.

Preferably the particles are applied by spraying onto a plurality of units in a coating drum. Improved results are obtained where the particles are in the form of a powder with a maximum particle size of about 250 microns or less, preferably about 150 microns or less, most preferably about 100 microns or less.

On startup drug loading is preferably preceded by a wetting of the non pareil seeds ensured by the binder/solvent. In operation the binding solution is preferably sprayed onto the units simultaneously with the application of the powder particles.

The process is particularly suitable for layering units such as non-pareil seeds where the substantially spherical form of the seed is retained to a high degree during layering with the result that each multi-layered dosage unit produced is substantially spherical.

Any suitable binder used in the preparation of pharmaceutical dosage forms can be used including for example polyvinylpyrrolidone, polyethylene glycol, polyvinyl alcohol, hydroxypropylcellulose, hydroxypropylmethylcellulose, hydroxyethylcellulose, methylcellulose, ethylcellulose, polyacrylates, carboxymethyl-cellulose or gelatine or mixtures thereof. Conveniently the binder is dissolved in a solvent to a suitable concentration. Where the powder being applied is sufficiently soluble in water (or other solvent) then the binder solution can consist solely of water (or other solvent) without added ingredient.

In a preferred embodiment this invention provides a process for preparing a multi-layered pharmaceutical seed unit which comprises the following steps:

a) loading inert nonpareil seeds into a suitable coating apparatus optionally electrostatically earthed,
b) dry spraying drug and/or excipient particles optionally electrostatically charged, onto the seeds using a spraying nozzle, while simultaneously applying a binding solution,
c) drying the loaded cores; to provide the multi-layered pharmaceutical seed unit.

This invention also provides apparatus for preparing said layered pharmaceutical seed units.

The apparatus comprises a vessel adapted to receive a seed unit, and loading means for layering said unit with particles, wherein said loading means comprises a powder spraying jet for dry spraying particles at said unit.

Optionally the powder layering may use an electrostatic potential difference to improve particle adhesion. This level of adhesion may be varied by adjusting the electrostatic charge. Preferably a plurality of seed units are provided.

Optionally, the powder layer can be sealed or coated in any known manner for example by using a final spray of liquid sealer, or by incorporating a waxy substance in the powder coating which is softenable on application of heat. The latter method may not be suitable if the active substance is heat sensitive.

Preferably the apparatus includes a fluid binder spray for ensuring adhesion of the particles to the units. Such a spray allows a build up of successive layers of particles on the units. The binder spray may be applied before, during or after spraying of the particles.

Separate spraying of powder and binder allows independent variation of flow rate and spray duration, which may be very useful in controlling process variables and permitting active control of the process according to real time measurements. The binder spray nozzle may also be used for spraying other coatings and/or sealing layers. Independent spray control also facilitates variation of the volume of liquid spray according to need, and to the size and absorbency of the seed units.

Ventilation of the coating vessel is preferred, especially where evaporation of liquid is required. In a preferred embodiment low pressure forced air ventilation is provided, and this allows further process control by variation of air pressure, flow rate and ventilation on/off periods. The ventilation air may also be pre-heated to a desirable level; this allows further control of process variables.

In the preferred embodiment, the layering vessel is a rotatable drum with a substantially horizontal axis in which is arranged a relatively fixed array of powder spraying nozzles. The drum preferably includes internal baffles or strakes to cause the seed units to roll and intermingle. In use rotation of the drum causes a charge of seed units to lie at one side, and preferably the powder spraying nozzles are orientated approximately at right angles to the surface plane of the charge. The orientation of the powder spraying nozzles may be adjustable. Real time adjustment may be provided in any suitable manner, for example by the use of stepper motors, pneumatics or the like.

Binder spray nozzles, where provided. may also have adjustable orientation in real time. The orientation of binder nozzles may be different from that of powder spraying nozzles, and the respective orientation may be independently variable. Where a plurality of nozzles of either type are provided, the nozzles may themselves be independently adjustable for flow rate orientation and spray pattern.

In the case of the rotatable drum, the powder spray nozzles and binder spray nozzles are preferably mounted from an end wall opposite to the usual door in the other end wall. A ventilation inlet duct may extend from one end close to the rotational axis of the drum. Radial duct arms preferably convey ventilation air close to the surface of the charge of seed units so as to blow air over the units. An exhaust outlet is preferably provided in the same end wall as the inlet.

The radial duct arms do not themselves disturb or suspend the seed units, as in prior art arrangements, and these arms may include end openings or diffusers of any suitable design, to ensure adequate air flow over the charge of units.

The distance between the powder spraying nozzles and the charges of seed units may be variable. Preferably this distance is variable in real time to ensure a desirable spraying pattern as the individual units grow in diameter and thus the charge volume increases, typically by 100% or more. The distance may be variable in discrete steps, or may be continuously variable according to desired process parameters. Any suitable means for moving individual nozzles, or a spray bar on which such nozzles are provided, may be adopted. Suitable means may be pneumatic or electrical; however the latter would be unacceptable in the case of solvent based binder sprays because of the risk of explosion. Variation of the distance between the binder spraying nozzles and powder spraying nozzles may be provided. Typically the powder spraying nozzle(s) are(is) from 70 mm to 250 mm in distance from the surface being sprayed, eg about 100 to 150 mm. Typically the binder spraying nozzle(s) are(is) from 150 mm to 450 mm in distance from the surface being sprayed, eg about 250 to 350 mm, preferasble about 300 mm.

The use of separate powder and binder spray nozzles is particularly useful because each can be independently adjusted with respect to orientation, flow rate, spray pattern, on/off time and distance from the units and from each other. This allows very close control of process parameters.

A further advantage of a horizontal axis drum is that a greater charge volume can be processed according to known process variables simply by increasing drum length and incorporating additional nozzles as required. This avoids the prior art solution of increasing drum diameter, which necessarily changes process variables in a manner which may be difficult to predict.

In a further aspect this invention provides a substantially spherical multi-layered dosage unit comprising one or more drugs, preferably having a shape factor (as hereinafter defined) of 0.65 or more; preferably greater than 0.8; most preferably 0.84 or more, e.g. at least 0.88.

Other features of the invention will be apparent from the following description of a preferred embodiment shown by way of example only in the accompanying drawings in which.

The following description refers to an embodiment in which the dry particles carry an electric charge. The apparatus is however also suitable for use with particles to which an electrostatic charge is not applied. or to which an electrostatic charge cannot be applied.

Figure 3:
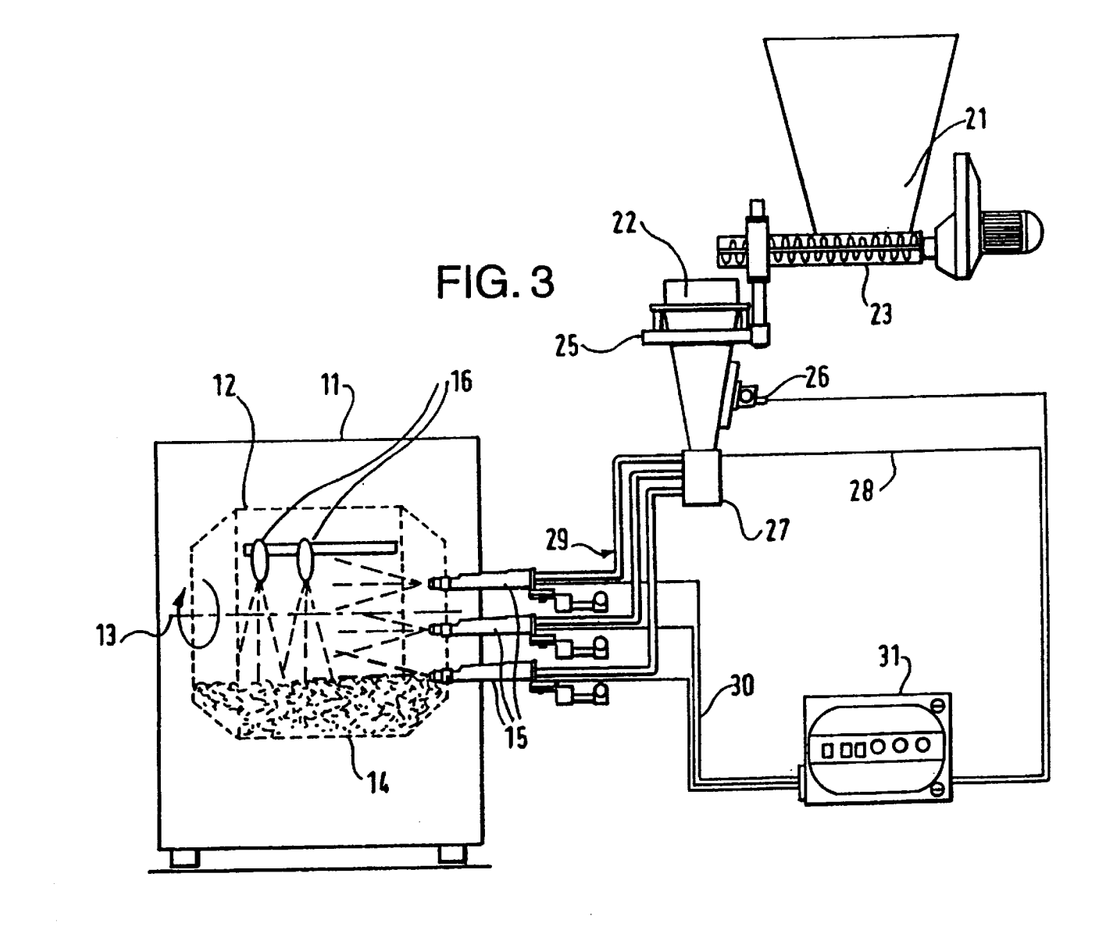
FIG. 3 is a schematic representation of apparatus according to the present invention.

A preferred arrangement of apparatus is illustrated in FIG. 3. A housing 11 contains a drum 12 rotatable about a horizontal axis 13 by a motor (not shown). The drum 12 has a door at one end (the left end as viewed) to allow a charge of seed units 14 to be loaded and unloaded. Within the drum, and mounted on a stationary end wall, are an array of powder spraying nozzles 15 and binder spraying nozzles 16. Ventilation apparatus (not shown in FIG. 3) is also mounted in the stationary end wall. and facilitates a flow of air through the drum for drying purposes.

The nozzles 15 may apply an electrostatic charge to the powder when required, as will be explained.

A bulk hopper 21 contains a supply of powder to be sprayed by the nozzles 15. Powder is supplied from the bulk hopper 21 to a supply hopper 22 by means of a screw feeder 23. The supply hopper 22 is suspended by weighing cells (not shown) on a fixed annular support 25. The cells calculate the weight of the hopper 22, and the speed of the screw feeder 23 is controlled to ensure that powder is supplied at a desired rate.

The supply hopper 22 has a vibrator 26 to ensure powder fluidity, and an injector 27 at the base thereof to which is connected an air line 28 for clean compressed air. Powder is entrained in the air supply and delivered to the powder nozzles 15 via supply lines 29. The nozzles 15 are also connected in electrical lines 30 to a control panel 31, for the purpose of applying the electrical charge to the powder if desired.

A binder solution is conveyed from a holding tank (not shown) by any suitable method to the binder nozzles 16. The compressed air, ventilation air, vibrator and binder solutions are also controlled via the panel 31.

Figure 4:
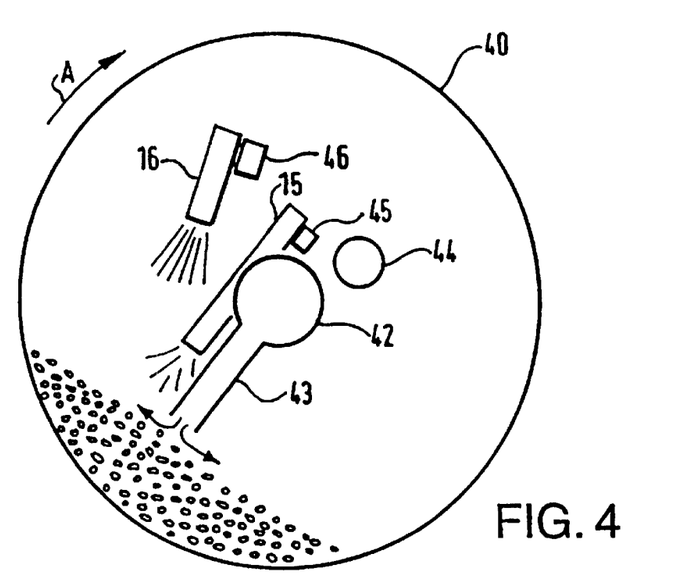
FIG. 4 is a schematic transverse section through a typical coating drum incorporating the invention.
Figure 5:
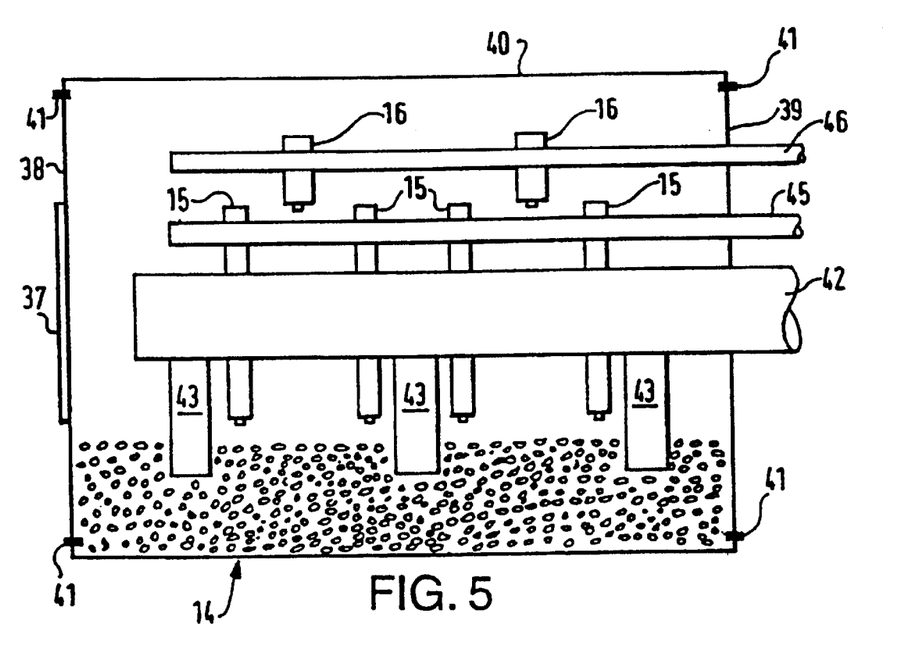
FIG. 5 is an axial section through the embodiment of FIG. 4.

FIGS. 4 and 5 illustrate a typical arrangement of components within a coating drum.

The drum 12 rotates in the direction of arrow A. As a result the inert cores 14 tend to pile up on the left side, as viewed. The drum includes discontinuous internal helical strakes (not shown) which ensure effective tumbling and rotation of the cores. The drum has a door 37, fixed ends 38, 39, a rotating barrel 40 and suitable seals 41.

An air supply duct 42 supplies ventilation air via hollow side arms 43. These side arms 43 direct air over the cores to facilitate drying. An exhaust outlet 44 is provided in one end of the drum. Three side arms 43 are illustrated, but more or less could be provided, as required.

A powder duct 45 supports and supplies four powder spraying nozzles 15; more or less nozzles could be provided according to circumstances. A binder solution duct 46 supports and supplies two binder spraying nozzles 16; again, more or less nozzles can be provided, as required.

The spray direction of nozzles 15 and 16 may be changed by, for example rotation of the respective supply ducts 45, 46. The nozzles may be mounted for movement towards and away from the cores, for example by pneumatic actuators.

In operation, a controlled weight of a drug in powder form is dispensed by the screw feeder 23 into the hopper 22 and in turn into the injector 27 connected with the air flow line 28. The air flow drives the powder particles to the application point where an electrode with an applied 100,000 volts creates an intense electrostatic field. As the powder passes through the electrostatic field each particle is given a negative charge. Charged particles are thus atomized through a nozzle onto the inert cores 14 placed into the drum 12. Simultaneously the binding solution is sprayed on to the cores by the separate nozzles 16. The inert cores are electrostatically neutral and exert a strong attraction to the highly charged drug particles which evenly coat all the exposed surfaces where they remain fixed by the binder after the evaporation of the binding solution solvent. As a result homogeneous drugs layers with excellent adherence and uniform thickness are obtained.

Electrostatic layering, performed by powder atomisation to ensure a continuative layering of drug particles without lag periods, further reduces the total manufacturing time in respect of traditional powder layering techniques.

However, maximum productivity varies depending on layering material flow characteristics. For this reason, powdery drugs having a particle size lower than 100 microns are preferred. Preferably the process object of the present invention has been developed according to the phases here below reported.

Loading the inert cores into a suitable coating drum

Spraying drug particles and/or excipients in powdery form onto the inert cores by using the electrostatic gun while simultaneously applying a binding solution.

Drying the loaded cores and providing them with a coating membrane by using conventional methods.

The process may also be run intermittently, i.e. addition of the binder solution may be started, followed by a short delay before the powder addition.

Drug particles having poor flowability may be sprayed in mixture with pharmaceutically acceptable excipients such as diluents, lubricants, glidants, etc. Alternatively the excipients may be layered separately before or after the drug loading.

To reduce agglomeration of the cores and improve the layering efficiency, both binder spray and powder addition rates need to be set conveniently depending on the drying system capacity. Evaporation conditions can be adjusted with the aid of a psychrometric chart Non pareils seeds are inert spherical solid particles, for example comprising sugar and corn starch. Those having a sieve cut ranging between 14 and 100 mesh are recommended. The rheological properties of a powdery drug are influenced dramatically by the particle size. Therefore in order to ensure a satisfactory flowability during the layering phases, actives with particle size ranging from about 10 to 100 microns are preferred. The drug applied to the inert core particles ranges on weight basis from about 9:1 to about 1:9; preferably from about 6:1 to about 1:6.

Drug loaded core sphericity is an important factor which affects a subsequent film coating. Coating on pellets having a near spherical shape and a smooth surface gives the best results in terms of process yields and reproducibility other than lowering the total amount of membrane to get the desired release profile. Drug loaded cores in the following examples were subjected to image analysis with a CIS 100 Particle Size and Shape Analyser (Galai Production Ltd, Israel).

Shape factor(S), the parameter selected to characterize the drug loaded cores, is a measure of the object sharpness. It is defined numerically by the following equation:

$$S=(Area/Perimeter^2) \times 4\pi$$

A value of 1 corresponds to a circle whereas values approaching 0 indicate straight lines. This measurement is useful in comparing the sphericity of drug loaded cores obtained with different layering processes.

Drug loaded pellets may be successively film coated with one or more polymeric membranes having controlled release, gastro resistance, targeted release or taste masking properties. A non-limiting illustrative list of coating polymers comprises: ethylcellulose, polyacrylates and polymethacrylates, polyvinylchloride, cellulose acetate, cellulose acetophthalate, hydroxypropylmethylcellulose phthalate, hydroxypropylmethylcellulose, hydroxypropylcellulose, waxes, polymers of natural origin such as shellac, gelatin, xanthan gum, arabic gun and mixtures thereof.

Film coating can be carried out according to known systems such as for instance pan coating, fluid bed coating or coacervation.

In the case of non-electrostatic coating, for example when using an organic binder solvent, the electric charging component is not activated, and accordingly non-charged powder is sprayed at the units.

The following non-limiting examples illustrate the invention:

EXAMPLE 1

A diclofenac composition was prepared according to two different manufacturing process, respectively:
(i) Powder layering
(ii) Powder layering with an electrostatic gun
The composition is set forth in Table I

TABLE I

| Ingredients | Quantity (%) |
|---|---|
| Diclofenac Sodium Salt | 43.5 |
| Non pareil seeds size 26 | 35.1 |
| Lactose G 200 | 3.3 |
| PEG 6000 | 7.5 |
| Talc | 10.5 |
| Tween 80 | 0.1 |
| Total | 100.0 |

(i) Powder Layering by Gravity (Traditional Method)

(a) 74.00 kg of non pareils seeds size 26 (600–800 $\mu$m) were loaded in a ventilated coating drum (Pellegrini GS 300) equipped with powder feeder, aircap spraying system (for binder solution) and peristaltic pump.

(b) Active mixture preparation 92.60 Kg of micronised diclofenac sodium salt having a particle size distribution lower than 100 $\mu$m, 22.40 Kg of Talc, 7.00 Kg of Lactose were passed through a 710 $\mu$m sieve. The components were than mixed in a 500 L cube for 20 minutes at 10 rpm.

(c) Binding solution preparation

In a 100 L tank with stirring system 16.00 Kg of PEG 6000 and 0.26 Kg of TWEEN 80 were dissolved at room temperature into 64.00 Kg of purified water.

Non pareils seeds size 26 were preheated at 30° C. then drug layering was carried out with discontinuous cycles. Drum speed was set at 15 rpm. Each layering cycle was performed as follows:

| | |
|---|---|
| spraying onto (a) an aliquot (156 g) of (c) | [rate: 4.46 g/sec.] |
| post spraying pause | [10 sec.] |
| powder layering via gravity feed onto (a) an aliquot (237 g) of (b) | [rate: 9.48 g/sec.] |
| post layering pause | [80 sec.] |
| drying (air capacity: 500 m³/h, air inlet temperature: 40° C.) | [60 sec.] |

Each cycle lasted a total of 210 seconds. 514 layering cycles for a total manufacturing time of 30 hours were necessary to terminate the drug loading onto the inert cores. Once the drug loading was terminated, the product was dried at 40° C. for 6 hours, then cooled at room temperature and sifted by 1180 $\mu$m sieve.

(ii) Electrostatic Powder Layering by Atomisation (a) 74 kg of non-pareils seeds size 26 (600–800 μm) were loaded on a ventilated coating pan (drum) (Pellegrini 300) equipped with powder feeder connected with an electrostatic gun, aircap spraying system and peristaltic pump.

(b) Quali-quantitative active mixture composition: the same as process (i)

(c) Quali-quantitative binding solution composition: the same as process (i)

Non pareils seeds size were preheated at 30° C. then drug layering was carried out with a continuous cycle. Pan speed was 15 rpm, the inlet air flow was 250 m$^3$/h, the temperature of the inlet air volume was 46° C. Steps (b) and (c) were carried out simultaneously by spraying the cores (a) respectively with the electrostatic gun and with the air cap spraying system, without resorting to intermediate drying phases as in process (i) above.

The average layering rates were the following:

(b): [3.85 g/sec]

(c): [2.53 g/sec]

The layering process lasted totally 528 minutes then the product was dried at 40° C. for 6 hours, cooled at room temperature and sifted through 1180 μm sieve.

Clearly layering can be performed during a daytime production run in this example, whereas the prior method required four to five shift working.

EXAMPLE 2

Diclofenac loaded pellets of Example 1 (i and ii) were successively characterised for powder layering efficiency and pellets sphericity. The superiority of process (ii) in comparison with process (i) is demonstrated by tha data reported in Table II.

TABLE II

| Process | Layering Processing Time (min) | Powder Layering Efficiency | | | Pellets Sphericity shape factor |
|---|---|---|---|---|---|
| | | weight yield[1] (%) | quantifiable weigh yield[2] (%) | drug loading[3] (%)/RSD | |
| (i) | 1800 | 89 | 94 | 91/3.5 | 0.6339 |
| (ii) | 528 | 96 | 99 | 95/1.1 | 0.8801 |

Figure 1:
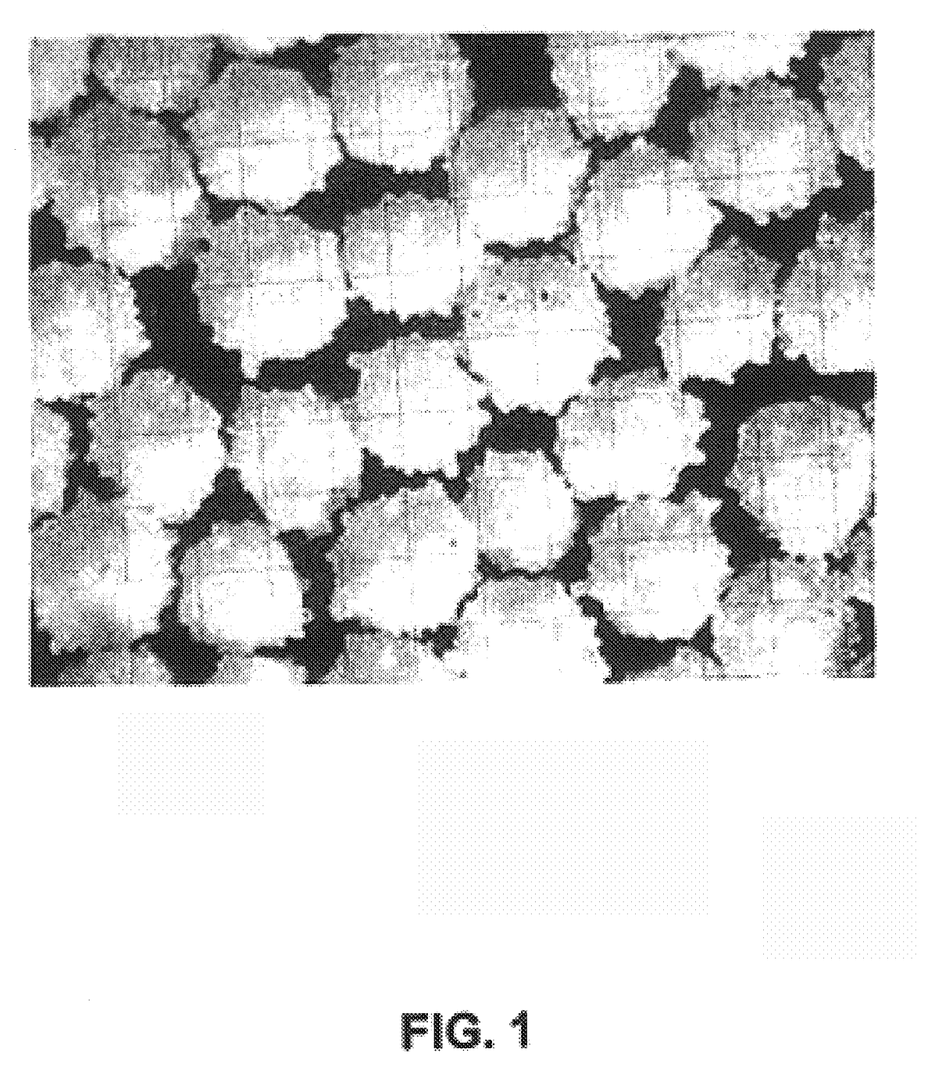
FIG. 1 is a photographic representation of seed units coated by a prior art powder layering technique.
Figure 2:
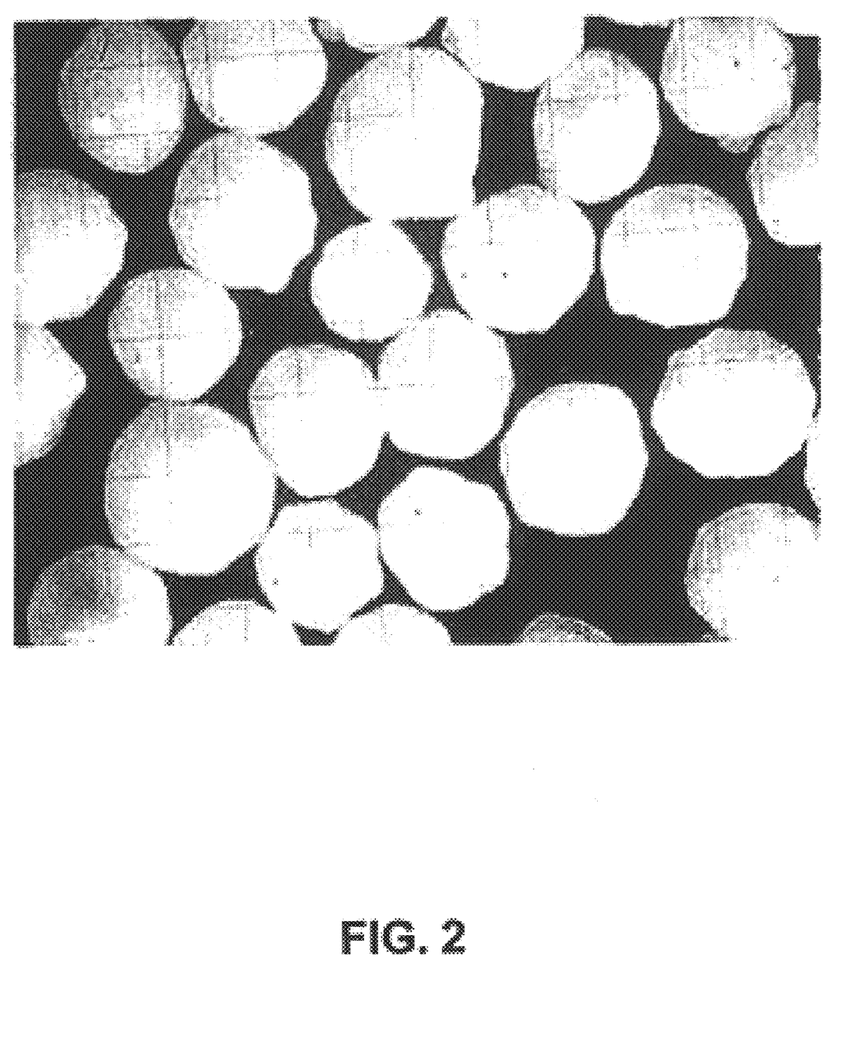
FIG. 2 is a photographic representation of a seed unit coated by a method according to the invention.

[1]product sifted by 1180 μm sieve.
[2]product recovered at the end of the process.
[3]calculated analytically as a percentage of drug layered in respect of the quantity used for powder layering. Drug loading uniformity onto the inert cores is expressed by the RSD (n = 10).
[1] and [2] were calculated as a percentage of product obtained in respect of the theoretical weight.
The difference represent the % of agglomerates (oversized rejects).
Pellets according to Example 1 (i and ii) are illustrated in FIGS. 1 and 2 respectively.

EXAMPLE 3

In the same equipment, diclofenac loaded pellets of example 1 (processes i and ii) were successively film coated by spraying a polymeric dispersion having the following composition (% by weight):

| | |
|---|---|
| Eudragit RL 100: | 4.64 |
| Talc micronised | 4.58 |
| PEG 6000 | 2.05 |
| Ethanol | 53.15 |
| Acetone | 35.58 |

The coating level on weight gain basis (% w/w of the dried components) was set forth in order to obtain diclofenac coated pellets showing the desired in vitro release profile. Drug releases were determined spectrophotometrically according to the following method: USP Apparatus II, Paddle, 900 mL pH 6.8, 125 rpm, 37° C. The release results in Table III represent the average of six replications.

TABLE III

| Diclofenac Loaded Pellets | Coating Level (weight gain % w/w) | Potency (mg/g) | Releases (%) | | | |
|---|---|---|---|---|---|---|
| | | | 30 min | 1 h | 2 h | 4 h |
| Ex. 1, process (i) | 4 | 408 | 53.6 | 76.9 | 95.6 | 101.4 |
| Ex. 1, process (ii) | 2.5 | 418 | 48.7 | 63.9 | 85.9 | 99.9 |

The results show that diclofenac loaded pellets obtained by powder layering with electrostatic gun (example 1, process ii), require a lower amount of membrane to obtain a release profile that is even lower than the one shown by the corresponding loaded pellets manufactured with the standard powder layering method (Example 1, process i).

What is claimed is:

1. A process for applying a layer to a pharmaceutical unit which comprises:

a) spraying the unit with dry particles of drug and/or excipient, wherein the unit and the particles are at different electrical potentials such that electrostatic attraction occurs between them;

b) applying to the unit a binder comprising a solvent;

c) drying;

d) film-coating the unit with one or more polymeric membranes having controlled release, gastroresistance, targeted release or taste masking properties.

2. A process as claimed in claim 1 in which the potential difference is from about 50,000 to about 300,000 volts.

3. A process as claimed in claim 1 wherein the unit is electrically neutral.

4. A process as claimed in claim 1, wherein particles are applied by spraying through an electrostatic field onto a plurality of units in a layering drum.

5. A process according to claim 1, wherein the particles and binder are applied to the unit from different directions.

6. A process according to claim 1, wherein the particles and binder are applied to the unit on separate axes, and in the same direction.

7. A process according to claim 1, wherein step (b) is initiated about 20 seconds or less before step (a) is initiated.

8. A process according to claim 1 carried out continuously by simultaneously performing steps (a) and (b) for a period sufficient to layer the desired amount of powder.

9. A process as claimed in claim 1 wherein the particles have a maximum size of about 250 microns or less.

10. A process as claimed in claim 1 wherein the particles have a maximum size of about 150 microns or less.

11. A process as claimed in claim 1 wherein the particles have a maximum particle size of about 100 microns or less.

12. A process as claimed in claim 1 wherein the unit is a non-pareil seed.

13. A process as claimed in claim 12 in which the non-pareil seeds have a sieve cut ranging from about 14 to about 100 mesh.

14. A process is claimed in claim 1 wherein the binder is polyvinylpyrrolidone, polyethylene glycol, polyvinyl alcohol, hydroxypropylcellulose, hydroxypropylmethylcellulose, hydroxyethylcellulose, methylcellulose, ethylcellulose, polyacrylates, carboxymethyl-cellulose or gelatine or mixtures thereof.

15. A process is claimed in claim 1 wherein the solvent is water.

16. A process as claimed in claim 1 comprising the following steps:
   a) loading inert nonpareil seeds into a suitable layering apparatus;
   b) dry spraying drug and/or excipient particles onto the seeds using a spraying nozzle with electrostatic attraction, while simultaneously applying a binding solution;
   c) drying the loaded cores during and after step (b);
   d) coating the drug loaded unit with one or more polymeric membranes having controlled release, gastroresistance, targeted release or taste masking properties.

17. A substantially spherical unit dosage form obtainable by a process according to claim 1.

18. A dosage form as claimed in claim 17, having a shape factor of 0.65 or more.

19. A dosage form as claimed in claim 17, having a shape factor of 0.8 or more.

20. A dosage form as claimed in claim 17, having a shape factor of 0.84 or more.

21. A dosage form as claimed in claim 17, having a shape factor of 0.88 or more.

* * * * *